United States Patent
Vacanti et al.

(10) Patent No.: US 6,176,874 B1
(45) Date of Patent: Jan. 23, 2001

(54) VASCULARIZED TISSUE REGENERATION MATRICES FORMED BY SOLID FREE FORM FABRICATION TECHNIQUES

(75) Inventors: Joseph P. Vacanti, Winchester; Linda G. Cima; Michael J. Cima, both of Lexington, all of MA (US)

(73) Assignees: Masschusetts Institute of Technology, Cambridge; Children's Medical Center Corporation, Boston, both of MA (US)

( * ) Notice: Under 35 U.S.C. 154(b), the term of this patent shall be extended for 0 days.

(21) Appl. No.: 08/477,226

(22) Filed: Jun. 7, 1995

Related U.S. Application Data

(63) Continuation-in-part of application No. 08/200,636, filed on Feb. 23, 1994, now Pat. No. 5,518,680, which is a continuation-in-part of application No. 08/138,345, filed on Oct. 18, 1993, now Pat. No. 5,490,962.

(51) Int. Cl.$^7$ .............................. A61F 2/00; A61C 27/56
(52) U.S. Cl. ................ 623/1.44; 623/1.41; 623/1.39; 623/901; 600/36
(58) Field of Search .................. 623/10, 16, 15, 623/1; 264/69, 25; 600/36

(56) References Cited

U.S. PATENT DOCUMENTS

| | | | |
|---|---|---|---|
| 4,046,513 | 9/1977 | Johnson | 23/253 TP |
| 4,060,081 | 11/1977 | Yannas et al. | 128/156 |
| 4,485,097 | 11/1984 | Bell | 424/95 |
| 4,520,821 | 6/1985 | Schmidt et al. | 128/334 R |
| 4,609,551 | 9/1986 | Caplan et al. | 424/95 |
| 4,620,327 | 11/1986 | Caplan et al. | 632/10 |
| 5,108,926 * | 4/1992 | Klebe | 623/15 |
| 5,197,985 | 3/1993 | Caplan et al. | 623/16 |
| 5,204,055 | 4/1993 | Sachs et al. | 419/2 |
| 5,226,914 | 7/1993 | Caplan et al. | 623/16 |
| 5,326,356 * | 7/1994 | Della Valle et al. | 623/15 |
| 5,387,380 * | 2/1995 | Cima et al. | 264/69 |
| 5,443,950 * | 8/1995 | Naughton et al. | 623/15 |

FOREIGN PATENT DOCUMENTS

| | | | |
|---|---|---|---|
| 0359575 * | 3/1990 | (EP) | 623/11 |

OTHER PUBLICATIONS

Boeree, N.R., et al., "Development of a degradable composite for orthopedic use: mechanical evaluation of an hydroxyapatite–polyhydroxybutyrate composite material," *Biomaterials*, 14:793–796 (1993).

Cima, et al., "Tissue Engineering by Cell Transplantation Using Degradable Polymer Substrates," J. Biomechan. Eng., 113:143–151 (1991).

Lee, J.H., J. Kopecek, et al., "Protein–resistant surfaces prepared by PEO–containing block copolymer surfactants," J. Biomed. Mat. Res., 23:351–368 (1989).

(List continued on next page.)

*Primary Examiner*—David H. Willse
*Assistant Examiner*—Choon P. Koh
(74) *Attorney, Agent, or Firm*—Arnall Golden & Gregory, LLP

(57) ABSTRACT

Solid free-form fabrication (SFF) methods are used to manufacture devices for allowing tissue regeneration and for seeding and implanting cells to form organ and structural components, which can additionally provide controlled release of bioactive agents, wherein the matrix is characterized by a network of lumens functionally equivalent to the naturally occurring vasculature of the tissue formed by the implanted cells, and which can be lined with endothelial cells and coupled to blood vessels at the time of implantation to form a vascular network throughout the matrix. The SFF methods can be adapted for use with a variety of polymeric, inorganic and composite materials to create structures with defined compositions, strengths, and densities, using computer aided design (CAD).

Examples of SFF methods include stereo-lithography (SLA), selective laser sintering (SLS), ballistic particle manufacturing (BPM), fusion deposition modeling (FDM), and three dimensional printing (3DP).

36 Claims, 4 Drawing Sheets

OTHER PUBLICATIONS

Martin, R.B., et al., "Bone ingrowth and mechanical properties of coralline hydroxyapatite one year after implantation," *Biomaterials*14:341–348 (1993).

Sachs, et al., "CAD–Casting:Direct Fabrication of Ceramic Shells and Cores by Three dimensional Printing" Manufacturing Review 5(2), 117–126 (1992).

Vacanti, et al., "Beyond Transplantation," *Arch. Surg.*, 123:545–549 (1988).

* cited by examiner

VASCULARIZED TISSUE REGENERATION MATRICES FORMED BY SOLID FREE FORM FABRICATION TECHNIQUES

This application is a continuation-in-part of U.S. Ser. No. 08/200,636, "Tissue Regeneration Matrices By Solid Free-Form Fabrication Techniques" filed Feb. 23, 1994 by Linda G. Cima and Michael J. Cima now U.S. Pat. No. 5,598,680, issued May 21, 1996 which is a continuation-in-part of U.S. Ser. No. 08/138,345, "Preparation of Medical Devices by Solid Free-Form Fabrication Methods" filed on Oct. 18, 1993 by Linda G. Cima and Michael J. Cima now U.S. Pat. No. 5,490,962, issued Feb. 13, 1996.

BACKGROUND OF THE INVENTION

The present invention is in the area of methods for formulating devices for tissue regeneration, which uses computer-aided design (CAD) in combination with solid free-form fabrication technology to form vascularized polymeric structures which can be implanted, seeded with cells, and form new tissue.

Strategies for regenerating tissue are being developed in response to a range of clinical needs, including replacement of damaged or genetically absent metabolic function from tissues such as liver, pancreas and pituitary tissue, and repair or restructuring of damaged or malformed connective tissues such as bone, cartilage and skin. Unlike blood or bone marrow tissues which can be regenerated by intravenous injection of cells, regeneration of most tissues requires a template.

New therapies for tissue regeneration include approaches in which cells are transplanted into a patient along with a device, and approaches in which a device is implanted next to normal tissue and guides the growth of that tissue into a new region. An example of the latter is a bone regeneration device placed into a fracture site, which guides growth of bone tissue into the fracture. Various materials are used to fabricate inorganic or inorganic/polymer matrices for bone regeneration. These include the coralline replaniform hydroxyapatite, which is essentially an adapted coral as described by Martin, R. B., et al., "Bone ingrowth and mechanical properties of coralline hydroxyapatite one year after implantation," *Biomaterials,* 14:341–348 (1993), and devices which incorporate a cellular component, as described by U.S. Pat, Nos. 4,620,327, 4,609,551, 5,226,914 and 5,197,985 to Arnold Caplan. Composite materials have also been described; however, they have been used primarily for fixation devices, and not bone ingrowth. See, for example, Boeree, N. R., et al., "Development of a degradable composite for orthopedic use: mechanical evaluation of an hydroxyapatite-polyhydroxybutyrate composite material," *Biomaterials,* 14:793–796 (1993).

Tissue engineering has emerged as a scientific field which has the potential to aid in human therapy by producing anatomic tissues and organs for the purpose of reconstructive surgery and transplantation. It combines the scientific fields of materials science, cell and molecular biology, and medicine to yield new devices for replacement, repair and reconstruction of tissues and structures within the body. Many approaches have been advocated over the last decade. One approach is to combine tissue specific cells with open porous polymer scaffolds which can then be implanted. Large numbers of cells can be added to the polymer device in cell culture and maintained by diffusion. After implantation, vascular ingrowth occurs, the cells remodel, and a new stable tissue is formed as the polymer degrades by hydrolysis. The diffusion distance for nutrients in vivo is only about 0.2 mm. Thus, a challenge in engineering structures thicker than 0.5 mm is to ensure an adequate supply of blood-borne nutrients, including oxygen (Cima, et al., *J. Biomechan. Eng.* 113, 143–151 (1991)).

A number of approaches have been described for fabricating tissue regeneration devices for either in vitro or in vivo growth of cells. Polymeric devices have been described for replacing organ function or providing structural support. Such methods have been reported by Vacanti, et al., *Arch. Surg.* 123, 545–549 (1988), U.S. Pat. No. 4,060,081 to Yannas, et al., U.S. Pat. No. 4,485,097 to Bell, and U.S. Pat. No. 4,520,821 to Schmidt, et al. In general, however, the methods used by Vacanti, et al., and Schmidt, et al., can be practiced by selecting and adapting existing polymer fiber compositions for implantation and seeding with cells, while the methods of Yannas and Bell produce very specific modified collagen sponge-like structures.

Tissue regeneration devices must be porous with interconnected pores to allow cell and tissue penetration. Factors such as pore size, shape and tortuosity can all affect tissue ingrowth but are difficult to control using standard processing techniques. U.S. Ser. No. 08/200,636, "Tissue Regeneration Matrices By Solid Free-Form Fabrication Techniques" filed Feb. 23, 1994 by Linda G. Cima and Michael J. Cima, described the use of solid free form fabrication techniques, especially three dimensional printing of polymer powders, to form matrices which could be seeded with dissociated cells and implanted to form new structures. The advantages of the solid free form methods to construct specific structures from biocompatible synthetic or natural polymers, inorganic materials, or composites of inorganic materials with polymers, where the resulting structure has defined pore sizes, shapes and orientations, particularly different pore sizes and orientations within the same device, with more than one surface chemistry or texture at different specified sites within the device, is readily apparent. However, the devices still have a major limitation: ingrowth of new tissue to form blood vessels which sustain the implanted cells must occur at the right time relative to the increasing cell density within the matrix to sustain the implanted cells, and other tissues must not encapsulate or infiltrate the matrix to choke out or otherwise destroy the implanted cells.

It is therefore an object of the present invention to provide methods and compositions for the preparation of polymeric matrices with complex, temporal and spatial patterns for use in tissue regeneration, which have predesigned vasculature, allowing the matrix to be implanted, connected to the existing blood supply, and immediately function as a new tissue or organ.

It is another object of the present invention to provide methods for culturing matrices seeded with cells so that lumens or other vessels are formed.

It is still another object of the present invention to provide matrices for tissue generation having pre-existing lumens and ducts within the matrix for exocrine, excretory, and other functions associated with normal tissue in vivo.

SUMMARY OF THE INVENTION

Solid free-form fabrication (SFF) methods are used to manufacture devices for allowing tissue regeneration and for seeding and implanting cells to form organ and structural components, which can additionally provide controlled release of bioactive agents, wherein the matrix is characterized by a network of lumens functionally equivalent to the naturally occurring vasculature of the tissue formed by the implanted cells, and which can be lined with endothelial cells and coupled to blood vessels or other ducts at the time of implantation to form a vascular or ductile network throughout the matrix. As defined herein, SFF refers to any manufacturing technique that builds a complex three dimensional object as a series of two dimensional layers. The SFF methods can be adapted for use with a variety of polymeric, inorganic and composite materials to create structures with defined compositions, strengths, and densities, using computer aided design (CAD).

Examples of SFF methods include stereo-lithography (SLA), selective laser sintering (SLS), ballistic particle manufacturing (BPM), fusion deposition modeling (FDM), and three dimensional printing (3DP). In a preferred embodiment, 3DP is used to precisely create channels and pores within a matrix to control subsequent, cell growth and proliferation in the matrix of one or more cell types having a defined function, such as hepatocytes, and to provide a vascular network lined with endothelial cells interspersed throughout the cells. Other structures can also be formed for use as lymph ducts, bile and other exocrine ducts, ureters and other excretory ducts.

The macrostructure and porous parameters can be manipulated by controlling printing parameters, the type of polymer and particle size, as well as the solvent and/or binder. Porosity of the matrix walls, as well as the matrix per se, can be manipulated using SFF methods, especially 3DP. Structural elements that maintain the integrity of the devices during erosion can also be incorporated. For example, to provide support, the walls of the device can be filled with resorbable inorganic material, which can further provide a source of mineral for the regenerating tissue. Most importantly, these features can be designed and tailored using computer assisted design (CAD) for individual patients to individualize the fit of the device.

BRIEF DESCRIPTION OF THE DRAWINGS

FIG. 4a is a 4× magnification of a matrix, looking down the channels of the channels seed with bovine endothelial cells, where the cells are lining the channels and beginning to round out the irregular square channels. FIG. 4b is a 10× magnification of two of the polymer channels, showing the cells forming round concentric layers within the channels. FIG. 4c is a 20× magnification of an endothelial lined channel of the three-dimensional polymer. FIG. 4d shows formation of "bridges" of hepatocytes lined on each side with blood vessels.

DETAILED DESCRIPTION OF THE INVENTION

Solid free-form fabrication methods offer several advantages for constructing medical devices for tissue engineering. Devices for tissue regeneration can be constructed to fit the individual patient, individual cell type or organ structure, and to include in the polymeric scaffolds the "skeleton" of a vascular system. Vascular endothelial cells as well as other components of the vascular bed can be added to the polymer template in vitro to form a vascular network which is intact and functional prior to implantation of the device. The rest of the device is sufficiently porous to allow the introduction of the other cell types necessary for the new tissue to be formed. The other cells can be implanted prior to, at the time of, or subsequent to implantation. The device can be tailored to the needs of individual patients.

SFF methods can be used to selectively control the composition within the build plane by varying the composition of printed material. Unconventional microstructures, such as those with complicated porous networks or unusual composition gradients, can be designed at a CAD terminal and built through an SFF process such as 3DP. Complex resorbable or erodible medical devices can be built which incorporate structural elements to insure the structural integrity of the device during erosion.

Figure 1A:
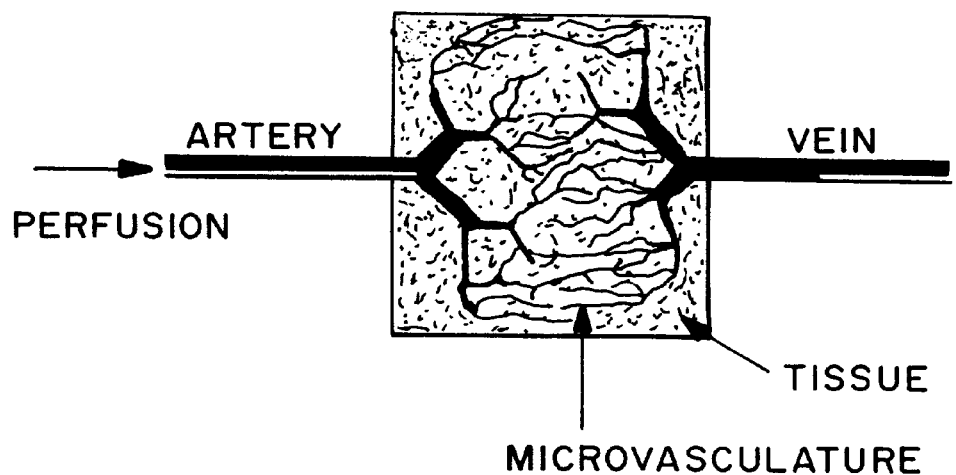
FIG. 1a is a schematic of the structure of the vascular network in tissue.
Figure 1B:
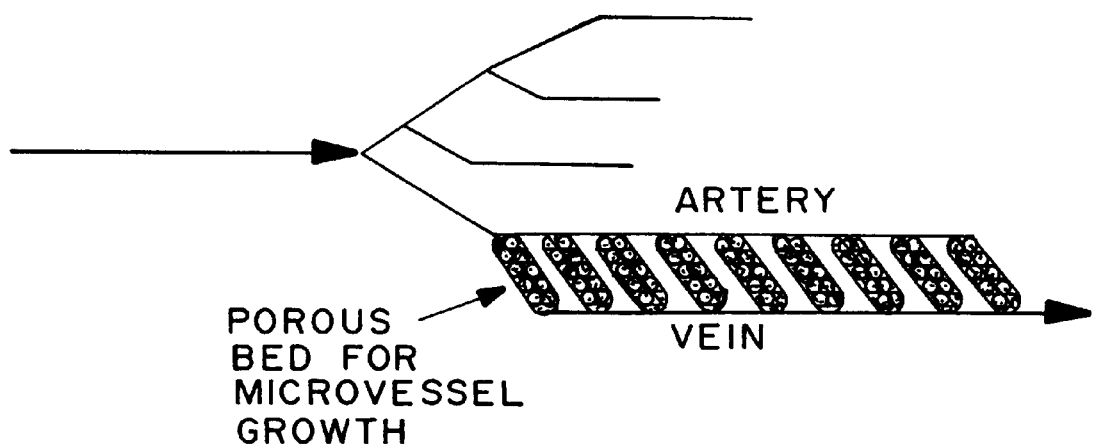
FIG. 1b is a schematic of a polymeric device anastomized to the vascular network in tissue.

Once designed and seeded with endothelial cells which have formed a continuous, intact, functional network, the matrix is implanted and fluid flow through the device established by anastomosis of the "neo-vessels" to appropriate blood vessels, tissues or ducts. For example, as shown in FIG. 1b, blood flow to the cells which is equivalent to the blood flow in normal tissue (FIG. 1a) can be achieved, thereby meeting the mass transfer requirements of the cells, regardless of the size of the matrix and number of implanted cells.

I. Solid Free Form Processes

Three Dimensional Printing (3DP).

3DP is described by Sachs, et al., "CAD-Casting Direct Fabrication of Ceramic Shells and Cores by Three Dimensional Printing" *Manufacturing Review* 5(2), 117–126 (1992) and U.S. Pat. No. 5,204,055 to Sachs, et al., the teachings of which are incorporated herein. Suitable devices include both those with a continuous jet stream print head and a drop-on-demand stream print head. A high speed printer of the continuous type, for example, is the Dijit printer made and sold by Diconix, Inc., of Dayton, Ohio, which has a line printing bar containing approximately 1,500 jets which can deliver up to 60 million droplets per second in a continuous fashion and can print at speeds up to 900 feet per minute. Both raster and vector apparatuses can be used. A raster apparatus is where the printhead goes back and forth across the bed with the jet turning on and off. This can have problems when the material is likely to clog the jet upon settling. A vector apparatus is similar to an x-y printer. Although potentially slower, the vector printer may yield a more uniform finish.

3DP is used to create a solid object by ink-jet printing a binder into selected areas of sequentially deposited layers of powder. Each layer is created by spreading a thin layer of powder over the surface of a powder bed. The powder bed is supported by a piston which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three dimensional structure. The unbound powder supports temporarily unconnected portions of the component as the structure is built but is removed after completion of printing.

As shown in U.S. Pat. No. 5,204,055, the 3DP apparatus includes a powder dispersion head which is driven reciprocally in a shuttle motion along the length of the powder bed. A linear stepping motor assembly is used to move the powder distribution head and the binder deposition head. The powdered material is dispensed in a confined region as the dispensing head is moved in discrete steps along the mold length to form a relatively loose layer having a typical thickness of about 100 to 200 microns, for example. An ink-jet print head having a plurality of ink-jet dispensers is also driven by the stepping motor assembly in the same reciprocal manner so as to follow the motion of the powder head and to selectively produce jets of a liquid binder material at selected regions which represent the walls of each cavity, thereby causing the powdered material at such regions to become bonded. The binder jets are dispensed along a line of the printhead which is moved in substantially the same manner as the dispensing head. Typical binder droplet sizes are between about 15 to 50 microns in diameter. The powder/binder layer forming process is repeated so as to build up the device layer by layer.

While the layers become hardened or at least partially hardened as each of the layers is laid down, once the desired final part configuration is achieved and the layering process is complete, in some applications it may be desirable that the form and its contents be heated or cured at a suitably selected temperature to further promote binding of the powder particles. In either case, whether or not further curing is required, the loose, unbonded powder particles are removed using a suitable technique, such as ultrasonic cleaning, to leave a finished device.

Construction of a 3DP component can be viewed as the knitting together of structural elements that result from printing individual binder droplets into a powder bed. These elements are called microstructural primitives. The dimensions of the primitives determine the length scale over which the microstructure can be changed. Thus, the smallest region over which the concentration of bioactive agent can be varied has dimensions near that of individual droplet primitives. Droplet primitives have dimensions that are very similar to the width of line primitives formed by consecutive printing of droplets along a single line in the powder bed. The dimensions of the line primitive depend on the powder and the amount of binder printed per unit line length. A line primitive of 500 $\mu$m width is produced if an ink jet depositing 1.1 cc/min of a solvent such as methylene chloride is made to travel at 8"/sec over a powdered polymer such as a polycaprolactone ("PLC") powder bed with between approximately 45 to 75 $\mu$m particle size. Higher print head velocities and smaller particle size produce finer lines. The dimensions of the primitive seem to scale with that calculated on the assumption that the liquid binder or solvent needs to fill the pores of the region in the powder which forms the primitive.

Finer feature size is also achieved by printing polymer solutions rather than pure solvents. For example, a 10 wt % PLC solution in chloroform produces 200 $\mu$m lines under the same conditions as above. The higher solution viscosity prevents slows the migration of solvent away from the center of the primitive.

The solvent drying rate is an important variable in the production of polymer parts by 3DP. Very rapid drying of the solvent tends to cause warping of the printed component. Much, if not all, of the warping can be eliminated by choosing a solvent with a low vapor pressure. Thus, PCL parts prepared by printing chloroform have nearly undetectable amounts of warpage, while large parts made with methylene chloride exhibit significant warpage. It has been found that it is often convenient to combine solvents to achieve minimal warping and adequate bonding between the particles. Thus, an aggressive solvent can be mixed in small proportions with a solvent with lower vapor pressure.

Stereo-lithography (SLA) and selective laser sintering (SLS).

SFF methods are particularly useful for their ability to control composition and microstructure on a small scale for the construction of these medical devices. The SFF methods, in addition to 3DP, that can be utilized to some degree as described herein are stereo-lithography (SLA), selective laser sintering (SLS), ballistic particle manufacturing (BPM), and fusion deposition modeling (FDM).

Stereolithography is based on the use of a focused ultraviolet (UV) laser which is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired device is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biocompatible polymeric materials.

SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tex.

SLA and SLS are thus similar in that in both techniques, matter is laminated to make three dimensional shapes. Use of these methods to control composition is limited to one dimensional control since one can only vary the composition of each layer. Nonetheless, these methods can be useful for construction of drug delivery and tissue matrix devices where one dimensional compositional control is all that is desired or where only variation in porosity is desired. Controlled porosity can be built using SLA and SLS simply by specifying the laser path over the layer surface to include only those regions which are to remain in the device.

However, SLA and SLS pose significant material constraints for the construction of tissue matrix preforms. SLA is limited to use with a photopolymerizable precursor that yields a biocompatible solid, such as UV or visible light curable acrylic systems used for bioadhesives, or a photo-curable material such as polyethylene oxide (PEO) precursors terminated with photo-crosslinking end groups. This process can be performed in the presence of sensitive biomolecules. Thus, structures can be built that incorporate drugs. Secondly, variation of the laser intensity or traversal speed can be used to vary the cross-link density within a layer so that the properties of the material can be varied from position to position with the part. SLS has the disadvantage that incorporation of sensitive biomolecules is difficult because of the need to locally heat the powder layer so as to sinter it. Nonetheless, highly porous structures can be built with low melting polymers, such as PEO powder. Variation of the laser intensity or traversal speed controls the degree of local densification. Thus, regions where the laser intensity is high or the traversal speed is low will have higher density.

Ballistic particle manufacturing (BPM) and Fusion deposition modeling (FDM)

BPM uses an ink-jet printing apparatus wherein an ink-jet stream of liquid polymer or polymer composite material is used to create three-dimensional objects under computer control, similar to the way an ink-jet printer produces two-dimensional graphic printing. The device is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y.

FDM employs an x-y plotter with a z motion to position an extrudable filament formed of a polymeric material, rendered fluid by heat or the presence of a solvent. A suitable system is available from Stratasys, Incorporated of Minneapolis, Minn.

BPM, FDM and 3DP are related in the sense that all three approaches deposit matter in small areas. Thus, they offer the advantage that local composition can be specified and constructed for any desired three dimensional profile. The composition control is only limited by the resolution of the particular apparatus used for construction. FDM builds structures by extruding a fine filament of plastically deformable material through a small nozzle. The nozzle is directed over the built surface by appropriate x, y and z motion control so as to yield the desired three dimensional structure. Similarly, BPM involves motion control of an ink jet print head to deposit matter in the form of small droplets. Appropriate control of where the droplets are printed permits the construction of a desired three dimensional shape. 3DP uses two sources of material: the material that makes up the porous layer and the material that is printed.

Local composition control using FDM and BPM requires the application of multiple printing or extrusion tools. A similar approach can be followed with 3DP by using multiple print-heads. Alternatively, multiple droplets may be printed into the same location when using 3DP to increase the local composition of the species contained in the printed solution.

Porosity control using BPM and FDM can be accomplished using procedures similar to those which can be practiced using 3DP, as described below.

II. Matrix Materials

Selection of Polymers

Depending on the processing method, the material forming the matrix may be in solution, as in the case of SLA, or in particle form, as in the case of SLS, BPM, FDM, and 3DP. In the preferred embodiment, the material is a polymer. In the first method, the polymer must be photopolymerizable. In the latter methods, the material is preferably in particulate form and is solidified by application of heat, solvent, or binder (adhesive). In the case of SLS and FDM, it is preferable to select polymers having relatively low melting points, to avoid exposing incorporated bioactive agent to elevated temperatures.

In the case of 3DP, a biocompatible material, preferably in particulate form, or as a porous sheet, is applied to a solid platform on a movable piston for solidification and/or incorporation of bioactive agent. A roller evenly spreads the particles over the platform bed. Solvent and/or binder is then selectively printed onto the polymer particles. After each layer is "printed", the piston lowers the polymeric material so that the process can be repeated to form the next layer.

The particles can be of any shape, including fibrous or rod shaped, although a more spherical particle will typically flow more smoothly. The particles are preferably in the range of ten microns or greater in diameter, although smaller particles can be used if spread in a liquid medium and allowed to dry in between printings.

A number of materials are commonly used to form a matrix. Unless otherwise specified, the term "polymer" will be used to include any of the materials used to form the matrix, including polymers and monomers which can be polymerized or adhered to form an integral unit, as well as inorganic and organic materials, as discussed below. In a preferred embodiment the particles are formed of a polymer which can be dissolved in an organic solvent and solidified by removal of the solvent, such as a synthetic thermoplastic polymer, for example, ethylene vinyl acetate, poly (anhydrides), polyorthoesters, polymers of lactic acid and glycolic acid and other $\alpha$ hydroxy acids, and polyphosphazenes, a protein polymer, for example, albumin or collagen, or a polysaccharide. The polymer can be non-biodegradable or biodegradable, typically via hydrolysis or enzymatic cleavage. Examples of non-polymeric materials which can be used to form the matrix include organic and inorganic materials such as hydroxyapatite, calcium carbonate, buffering agents, and lactose, as well as other common excipients used in drugs, which are solidified by application of adhesive or binder rather than solvent. In the case of polymers for use in making devices for cell attachment and growth, polymers are selected based on the ability of the polymer to elicit the appropriate biological response from cells, for example, attachment, migration, proliferation and gene expression.

Photopolymerizable, biocompatible water-soluble polymers include polyethylene glycol tetraacrylate (Mw 18,500) which can be photopolymerized with an argon laser under biologically compatible conditions using an initiator such as triethanolamine, N-vinylpyrrolidone, and eosin Y. Similar photopolymerizable macromers having a poly(ethylene glycol) central block, extended with hydrolyzable oligomers such as oligo(d,l-lactic acid) or oligo(glycolic acid) and terminated with acrylate groups, may be used.

Examples of biocompatible polymers with low melting temperatures include polyethyleneglycol 400 (PEG) which melts at 4–80° C., PEG 600 which melts at 20–25° C., and PEG 1500 which melts at 44–480° C. Another low melting material is stearic acid, which melts at 70° C.

Other suitable polymers can be obtained by reference to The Polymer Handbook, 3rd edition (Wiley, N.Y., 1989), the teachings of which are incorporated herein.

A preferred material is a polyester in the polylactide/polyglycolide family. These polymers have received a great deal of attention in the drug delivery and tissue regeneration areas for a number of reasons. They have been in use for over 20 years in surgical sutures, are Food and Drug Administration (FDA)-approved and have a long and favorable clinical record. A wide range of physical properties and degradation times can be achieved by varying the monomer ratios in lactide/glycolide copolymers: poly-L-lactic acid (PLLA) and poly-glycolic acid (PGA) exhibit a high degree of crystallinity and degrade relatively slowly, while copolymers of PLLA and PGA, PLGAs, are amorphous and rapidly degraded. Although attempts have been made to develop true surface-eroding polymer, for example, polyanhydrides, the relationship between polymer composition and device properties are very difficult to control in practice by standard fabrication techniques. These problems are avoided using the processing technology described herein.

For microstructures tailored to bone, inorganic powders in the final device increase the strength of the device and provide a source of minerals for the regenerating tissue. The strength requirements of soft tissues such as liver are substantially less than for bone, so greater void fractions in the final devices can be tolerated.

Although these devices can be created by any of the SFF techniques, the preferred method is 3DP. In one approach, an inorganic powder is spread in the bed. This powder will generally be some form of calcium phosphate or hydroxyapatite and can be derived from natural sources (i.e., isolated from animal bones) or synthetically created powder. If the powder is isolated from bone (for example, by grinding bone in a Glenn Mills Milling machine), it may not be strictly inorganic but may contain natural proteins and other biological macromolecules. The powder is preferably resorbable or biodegradable. The powder size controls the resolution of the wall thickness and the layer thickness. Powders less than 40 microns in diameter are preferred in order to obtain resolutions of less than 100 microns. Resolution is generally at least twice the dimension of the powder size. Very fine powders, typically less than one micron in diameter, may be spread into the bed as a solution which is then allowed to dry, or such powders can be formed into thin, generally between 100 and 200 micron thick, coherent, porous sheets by non-specific interactions in a separate step outside the 3DP machine, and the resulting sheets can be laid in the bed as each layer is built up as an alternative to the normal rolling and spreading operation. Layers are preferably at least between 2 and 5 microns in thickness, more preferably 10 to 20 microns, and more typically between 100 microns and 1 mm. Bone derived apatite is an example of an inorganic powder which can be processed in this manner. Bone derived apatite has particles of average dimensions 0.003×0.009×0.04 microns.

Selection of Binder

Solvents and/or binder are used in the preferred method, 3DP, as well as SLA and BPM.

The binder can be a solvent for the polymer and/or bioactive agent or an adhesive which binds the polymer particles. Solvents for most of the thermoplastic polymers are known, for example, methylene chloride or other organic solvents. Organic and aqueous solvents for the protein and polysaccharide polymers are also known, although an aqueous solution, for example, containing a crosslinking agent such as carbodiimide or glutaraldehyde, is preferred if denaturation of the protein is to be avoided. In some cases, however, binding is best achieved by denaturation of the protein.

The binder can be the same material as is used in conventional powder processing methods or may be designed to ultimately yield the same binder through chemical or physical changes that take place in the powder bed after printing, for example, as a result of heating, photopolymerization, or catalysis.

The selection of the solvent for the bioactive agent depends on the desired mode of release. In the case of an erodible device, the solvent is selected to either dissolve the matrix or is selected to contain a second polymer and/or a drug which is deposited. In the first case, the printed droplet locally dissolves the polymer powder and begins to evaporate. The drug is effectively deposited in the polymer powder after evaporation since the dissolved polymer is deposited along with the drug. The case where both the drug and a polymer are dissolved in the printed solution is useful in cases where the powder layer is not soluble in the solvent. In this case, binding is achieved by deposition of the drug polymer composite at the necks between the powder particles so that they are effectively bound together.

Aggressive solvents tend to nearly dissolve the particles and reprecipitate dense polymer upon drying. The time for drying is primarily determined by the vapor pressure of the solvent. There is a range from one extreme over which the polymer is very soluble, for example, 30 weight percent solubility, which allows the polymer to dissolve very quickly, during the time required to print one layer, as compared with lower solubilities. The degree to which the particles are attacked depends on the particle size and the solubility of the polymer in the solvent. Fine powder is more completely dissolved than powder with larger particle size.

Binders and Polymer Concentration

The binder can be a resorbable polymer such as polylactic acid or polycaprolactone of molecular weight 50,000–200,000, in a solvent such as chloroform or a mixture of chloroform and a less-volatile solvent such as ethyl acetate to minimize warping.

The matrix material concentration in the binder solution will generally be at the limit of what can be accommodated by the nozzle, both to maximize the amount of matter delivered and to minimize migration of the solvent away from the ballistic impact point of the drop, thereby maximizing the resolution of the line width. The upper limit of polymer concentration is 15% for poly-L-lactic acid of 100,000 MW. This concentration of polymer may in some cases be insufficient in one-pass printing; devices made with larger powders may be cohesive with this amount of polymer. The amount of matter printed can be increased by including small latex or other particles in the printing solution. For example, polyglycolic acid (PGA) is not soluble in chloroform or ethyl acetate. Nanoparticles of PGA could be included in the printing solution (particles up to seven microns in diameter can be accommodated through the nozzle) to increase the polymer content which is printed. Latexes containing 30% by weight polymer (Eudragit™ are commercially available acrylic latexes) have been printed in existing machines without complications.

The amount of matter which is printed into the bed can also be increased by including small inorganic particles in the polymer solution, for example, bone derived apatite.

Another approach to increasing the amount of polymer printed in the bed is to print a second or more passes after the first layer has at least partially dried before moving to the next layer.

Means for Altering Texture of Device Features

A "wall", for example, a feature 100 microns thick by 1 cm×1 cm, will exhibit different textures if it is built by printing a single line layer after layer after layer up through the depth of the bed, as compared to printing a sheet of contiguous lines within one layer. The wall built up by printing a line layer after layer will have texture on both sides (some of the powder will adhere), and that texture will be identical on each side. In contrast, a sheet printed using contiguous lines within the same layer will in most cases have different textures on each side. The "bottom" will have a texture influenced by incomplete assimilation of the powder into the bulk of the polymer wall. The "top" can be smooth, because more binder is inherently trapped in the top of the printed line, covering up the particles. However, at low polymer concentrations in the printed binder, the top of the "sheet" can also exhibit significant texture since the binder is less viscous and can penetrate into the powder more easily.

The texture in a sheet is influenced both by the binder concentration in the powder and by the spacing between contiguous lines. For example, a 15% PCL solution in chloroform printed into PCL powder with 75–100 micron powder size using a printing speed of 4–12 cm/s will form a smooth layer if printed at a spacing of 25 microns but will form a highly textured surface if printed at a spacing of 75 microns.

These effects of texture can be beneficial in designing devices to get optimal tissue regeneration rates. A single channel of square cross-section can have smooth surfaces on one or two sides and textured surfaces on the other. Smooth surfaces can allow rapid cell migration, while textured surfaces can provide a site for cells to differentiate.

Formation of Composite Devices

Composite devices can be made by combining inorganic and organic components. In particular, it may be desired to increase the amount of matrix material in the device above that which can be obtained by one-pass printing of a solution of a matrix material into an inorganic powder bed, for example, by adding a polymer latex to the printing solution. Another method is to mix a polymer powder with an inorganic powder. Still another method is to spread only polymer powder in the bed, and print a dispersion of inorganic particles (up to 30 vol %) in a solvent which will bind the polymer powder together. An example of this is to print a solution of apatite particles in chloroform onto a PLA powder bed. Alternatively one can include a polymer binder with an inorganic dispersion, for example by adding 30% by volume particles to a 5% by weight solution of PLA in chloroform. In the extreme, the bed could contain no material at all; both the inorganic and organic material could be printed through the nozzle.

Bioactive agents which can be incorporated.

There are essentially no limitations on the bioactive agents that can be incorporated into the devices, although those materials which can be processed into particles using spray drying, atomization, grinding, or other standard methodology, or those materials which can be formed into emulsifications, microparticles, liposomes, or other small particles, and which remain stable chemically and retain biological activity in a polymeric matrix, are preferred.

Bioactive agents also include compounds having principally a structural role, for example, hydroxyapatite crystals in a matrix for bone regeneration. The particles may have a size of greater than or less than the particle size of the polymer particles used to make the matrix.

Examples generally include proteins and peptides, nucleic acids, polysaccharides, nucleic acids, lipids, and non-protein organic and inorganic compounds, referred to herein as "bioactive agents" unless specifically stated otherwise. These materials have biological effects including, but not limited to, anti-inflammatories, antimicrobials, anti-cancer, antivirals, hormones, antioxidants, channel blockers, and vaccines. It is also possible to incorporate materials not exerting a biological effect such as air, radiopaque materials such as barium, or other imaging agents.

In a preferred embodiment for tissue regeneration matrices, cell growth, differentiation, and/or migration modulators are incorporated into specific regions of the device at the same level of resolution as the pores and channels. These materials are commercially available from suppliers such as Sigma Chemical Company, and have been extensively described in the literature.

Patterns for Incorporation of Bioactive Agent

There are two principle methods for incorporation of bioactive agents: as a dispersion within a polymeric matrix and as discrete units within a discrete polymeric matrix. In the first case, the bioactive agent is preferably applied in the polymer particle binder; in the second, the bioactive agent is applied in a non-solvent for the polymer particles.

In the case of SLA, bioactive material to be incorporated is dispersed into the liquid matrix material; in all other cases, bioactive material to be incorporated can be mixed with the particles, although this can result in a significant waste of the material in the case of SLS and 3DP; in these cases it is preferable to incorporate the bioactive material into the solvent or binder.

For example, the devices can be composed of particles of bioactive agent dispersed or embedded in a matrix of degradable polymer, such as PLA, PGA, and their copolymers (PLGAs). Implantation of the device is followed by slow hydrolysis and erosion of the polymer matrix. The release rate of bioactive agent is determined by the erosion rate of the polymer rather than just diffusion. Thus, the drug release rate can be controlled by the distribution of the drug throughout the matrix or by variation of the polymer microstructure so that the erosion rate varies with the position in the device. A drug concentration profile that is periodic with position away from the device surface will, for example, yield a drug release rate that is periodic in time as the polymer is eroded. The same effect can be achieved by periodic variation in polymer composition or porosity.

In another embodiment, a bioactive agent can be incorporated by adsorption onto the surface of the structural polymer during fabrication in the following way: print a line of binder (for example, chloroform for poly(L-lactic acid) (PLLA)), then adjacent to the line print a line of aqueous solution with a fibroblast growth factor (FGF)-heparin angiogenic factor mixture in it. The FGF-heparin will adsorb out of the solution onto the polymer surface to locally provide the angiogenic factors.

Incorporating Structural Elements

Practical application of erodible devices is limited by the mechanical integrity of the device during the course of erosion. Real erodible devices do not decompose by simple surface limited reactions. Rather, the surface and bulk microstructure evolve during the course of erosion and alter the rate at which the drug is delivered. For example, oral erodible devices pit and break apart, which modifies the surface area exposed to the fluid and changes the rate at which drug is released. Resorbable polymer devices swell before hydrolysis which also causes nonlinear release of the drug.

Structural elements made using the same or different polymeric particles can be designed within the device to provide physical structural support during degradation so as to avoid many of the problems associated with erodible devices. 3DP is used to create structural elements within the device formed by the solidification of the polymer particles, for example, by deposition of areas or regions of a different polymeric material, such as regions of a non-degradable polymer within regions of a degradable polymer.

Controlling Porosity in Devices.

Porosity in 3D printed devices can be created either at the level of the feature size (between 10 and 20 microns and greater) or at a sub-feature size level. At the level of the feature size, porosity is controlled by where the features are placed, and thus pore size and shape can vary in three dimensions.

Porosity at a subfeature size level can be created in a variety of ways.

(1) Printing a polymer solution onto a bed of particles which are not soluble in the polymer and which can be subsequently leached with a non-solvent for the polymer. In this case, the polymer which forms the device is printed onto a bed of particles such as salt, sugar, or polyethylene oxide. After the printing process is complete, the device is removed from the powder bed and placed in a nonsolvent for the polymer which will dissolve the particles. For example, polylactic acid in chloroform could be printed onto a bed of sugar particles, and the sugar can subsequently be leached with water.

(2) Printing a polymer solution onto a bed of particles which are partially soluble in the printed solvent. An example is printing a polylactic acid solution onto a bed of polyethylene oxide particles. This procedure may allow interpenetration of PEO into the surface of the PLA and improve surface properties of the final device. Following printing, the PEO can be leached with water.

(3) Printing a polymer solution onto a heated bed of polymer. An example is printing polylactic acid in chloroform onto a bed of PLA particles heated to 100° C. The boiling point of chloroform is 60° C., and it will thus boil on hitting the particle bed, causing a foam to form.

(4) Printing a polymer solution onto a bed containing a foaming agent.

(5) Printing with solvents which have only a small solubility for the powder. In this manner only a small amount of polymer is deposited at the necks between the particles leaving much of the original porosity in the powder bed. For example, PCL is only slightly soluble in acetone and acetone has a relatively high vapor pressure. Very little polymer is, therefore, dissolved before the solvent dries. Thus, the necks formed between the particles are small and the porosity of the resulting component is much like that of the original powder bed.

Devices having modified surface properties.

Modifying surface properties in select regions of the device is also important and can be accomplished by printing a solution containing surface-active agents into the regions or lines in between where the binder is printed. As used herein, a "surface-active agent" may be an agent which promotes cell adhesion, such as an RGD peptide, or a material which inhibits cell adhesion, such as a surfactant, for example, polyethylene glycol or a Pluronic™ (polypropylene oxide-polyethylene oxide block copolymers). The surface-active agent should in general be contained in a solvent immiscible with the solvent used to print the binder.

For example, it may be desirable to incorporate adhesion peptides such as the RGD adhesion peptide into certain channels (e.g., those for blood vessel ingrowth). An adhesion peptide, such as the peptide having a hydrophobic tail marketed by Telios (LaHoya, Calif. as Peptite™, can be dissolved in water and printed into the "voids" using a second set of printing nozzles. Adding water, a relatively non-volatile solvent, can alter the kinetics of solvent removal from regions printed with binder. For example, adding water can slow solvent removal by occluding the surface area for evaporation, and can help decrease warpage. On contact with the polymer surface, the peptide will adsorb out of solution onto the polymer surface.

The surface can also be modified to prevent cellular adhesion. This may be desirable to prevent excessive soft connective tissue ingrowth into the device from the surrounding tissue, and can be accomplished, for example, by printing an aqueous solution of a pluronic™ (BASF) or poloxamer™ in the voids. The hydrophobic block of such copolymers will adsorb to the surface of the channels, with the hydrophilic block extending into the aqueous phase.

Surfaces with adsorbed pluronics™ resist adsorption of proteins and other biological macromolecules. Other adhesion-preventing materials are described in Lee, J. H., J. Kopecek, et al., "Protein-resistant surfaces prepared by PEO-containing block copolymer surfactants." *J. Biomed. Mat. Res,* 23:351–368 (1989), the teachings of which are hereby incorporated by reference.

Printing the device with surface active agents while the "walls" of the device are still "wet" with organic solvent (such as chloroform) can enhance the adsorption of the adhesion-preventing material to the walls and can even allow the hydrophobic block to become blended into the surface, enhancing the stability of the resulting surface modification.

Figure 2:
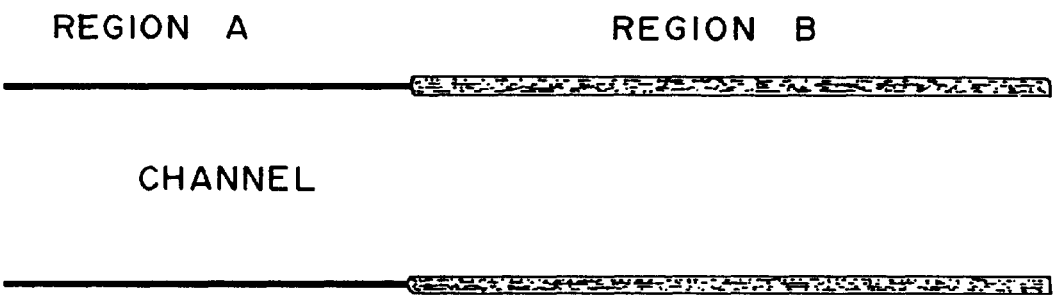
FIG. 2 is a schematic of the construction of a device having a Region A of a polymer (PLLA) channel printed with general cell adhesion molecules to enhance cell adhesion, while region B is printed with a surfactant to inhibit cell adhesion.

Cells can be positioned at specific sites in the matrix by using selective surface chemistries locally. Referring to FIG. 2, cells can be targeted to specific sites within the matrix in any of several ways:

(1) Region A of a polymer (PLLA) channel is printed with a general cell adhesion molecules such as fibronectin, collagen, or laminin, to enhance cell adhesion, while region B is printed with a surfactant such as Pluronic® 68 (polyethylene oxide-polypropylene oxide block copolymers) to inhibit cell adhesion. Printing the surface modifiers can be accomplished by printing an aqueous solution of the desired surface modifier in a line next to the binder line printed to form the channel. The protein or surfactant will adsorb from the aqueous solution to the surface of the polymer. Alternatively, the surface modifier can be included with the binder itself. Surfactants, including proteins, can modify surface properties when included at very low concentrations in the binder, 0.1 to 1% by weight. At these concentrations, changes in the bulk properties are small. At an initial time, parenchymal cells are seeded and adhere in region A while no cells adhere in region B. After approximately one to two weeks of culture, endothelial cells or another cell type can be seeded on top of the parenchymal cells. Region B can be modified prior to seeding the second cell type by treating with an aqueous solution of an adhesion protein such as fibronectin, which can displace the surfactant and thus enable cell adhesion in regions where it was previously inhibited to allow a complete coating by endothelial cells on all interior surfaces of the matrix.

(2) Region A can be printed with a molecule which is selective for one cell type and Region B with a molecule selective for another cell type. Such molecules will generally include a highly specific small ligand, such as REDV for endothelial cells or galactose for hepatocytes, linked to a strong hydrophobic moiety (such as than in Cell-Tak, a commercially available reagent) which will adsorb strongly to the surface of PLLA and poly(lactic acid-glycolic acid) (PLGA). This allows spatial segregation when seeding more than one cell type at the initial time.

III. Constructing Preforms for Tissue Engineering

Regeneration of native tissue structures can occur by stimulation of growth of neighboring, healthy tissue (e.g., healing a defect in bone) or may require transplantation of cells from another site, using either the patient's own tissue or that of a tissue-matched donor (e.g., growth of a new cartilage structure, replacement of liver). In either case, a device which serves as a scaffold or template to aid the growth of the new tissue is almost always necessary. The device can serve many functions, including: (1) as an immobilization site for transplanted cells, (2) formation of a protective space to prevent soft tissue prolapse into the wound bed and allow healing with differentiated tissue, (3) directing migration or growth of cells via surface properties of the device, and (4) directing migration or growth of cells via release of soluble molecules such as growth factors, hormones, or cytokines.

For the three applications described above, as well as for other applications in tissue regeneration which can be envisioned, 3DP offers at least three advantages over current technologies for processing biodegradable polymers: (1) tailored macroscopic shapes, (2) well-defined microstructure, which may include bimodal pore size distribution and directionally oriented pores and channels, (3) incorporation of growth factors during manufacture in order to provide controlled release of factors at specific sites, and (4) the ability to locally control surface properties in selected pores and channels to control cell adhesion, migration, and function from point to point within the device.

As used herein, "tissue" includes both soft tissues such as parenchymal tissue (liver, pancreas, intestine, and other tissues having metabolic functions), blood vessels, skin, and connective tissues such as cartilage and bone.

Although matrix construction varies with each tissue type, the methods used for construction will typically be the same, optimized to create appropriate shapes and pore sizes and lumens for blood and other vessels, including vessels for lymph, nerve, exocrine and excretory functions. Virtually all tissues require lymph drainage. Other specific duct structures include bile ducts in liver, mammary ducts in breast, and tubules in kidney. These duct structures have in common a gradation in size of the vessels from small (2–50 micron) vessels which permeate the tissue to large collecting ductules 1 mm or more in diameter, and the duct structure is typically branched. The branched structures may also serve for nerve ingrowth.

In general, interconnected pores or channels will extend from the exterior throughout the interior, typically between 0.15 and 0.5 mm in diameter, which are separated by walls approximately 30 to 300 microns thick, which are either solid or porous with an average pore size of approximately 5 to 80 microns. The particular placement of vessels within the matrix depends on the tissue being perfused. In tissues which are highly metabolically active, such as liver, cells are no more than one or two cell layers away from the blood stream, a distance of ten to twenty microns. At the other extreme, there are no blood vessels in healthy cartilage, which may be 1 mm or more thick. Tissues such as bone are intermediate, where cells are distributed sparsely in space and relatively calm metabolically. The volumetric consumption rate of oxygen by metabolically active cells, $Q_{oxygen}$, is about $3 \times 10^{-5}$ mmol/cm$^3$ cell mass-s (Cima, Ph.D. thesis, University of California at Berkeley, Chemical Engineering 1988), where the cell mass is considered "close-packed". In a tissue like cortical bone, the fraction of cells in the tissue volume is only about 10%, and the $Q_{oxygen}$ is correspondingly reduced when calculated on a tissue basis (i.e., the tissue consumption rate would be about $0.3 \times 10^{-5}$ mmol/cm$^3$ cell mass-s). The flow rate of blood or culture medium required to supply a tissue with adequate oxygen (the limiting nutrient) is then $$F = 2 \left[ \frac{Q_{oxygen}}{c_{oxygen}} \right] V_{cellular\ tissue}$$

where F is the volumetric flow rate, $Q_{oxygen}$ is the volumetric consumption rate of oxygen, $c_{oxygen}$ is the concentration of oxygen in the artery leading to the tissue, and $V_{cellular\ tissue}$ is the volume of the tissue element, not including the blood volume itself. The supply of oxygen is "adequate" if the concentration of oxygen in the vein leading away from the tissue is at least 50% of the concentration of the oxygen in the artery; this leads to the prefactor of 2. For standard tissue culture medium saturated with air, $C_{oxygen} = 0.16 \times 10^{-3}$ mmol/ml (Cima, Ph.D. thesis). For blood, the concentration is higher due to the presence of hemoglobin, and in arterial blood $c_{oxygen}$ is approximately $0.8 \times 10^{-3}$ mmol/ml. Thus, for liver, a medium flowrate of 23 ml/min is required per cm$^3$ of tissue, and the corresponding required blood flow rate is about 4 ml/min per cm$^3$ of tissue. For bone, these flow rates are about 2 and 0.4 ml/min, respectively.

The placement of channels to provide conduits for appropriate distribution of blood flow must take into consideration (1) the available pressure drop driving force and (2) the diffusion distance. If the fraction of a tissue which is cellular by $\alpha$ (for example, bone is $\alpha = 0.1$) is designated, then the thickness of a tissue layer which can be supported by blood or medium flowing through any diameter channel is about $50/\alpha$ microns, since the diffusion distance of oxygen in "close packed" tissue is about 50 microns. Using 3-DP or other similar SSF technology for biodegradable polymers such as polyester, oriented channels 150 microns in diameter and micropores on the order of 3 to 50 microns can be created using excipients in the powder bed. FIG. 1a is a schematic of the normal vasculature of tissue. One approach to creating the appropriate tissue architecture in vitro is to construct a branching system as shown in FIG. 1b, where the dark lines designate channels created in the matrix. The shaded regions represent areas printed with a material that resorbs more rapidly than the surrounding matrix. To create a tissue in vitro, the device is first seeded with a layer of parenchymal cells. This layer can be maintained in culture for a week or so in order to obtain a population doubling. It can be maintained in a perfusion reactor to ensure adequate oxygen supply to the cells in the interior. The device is then seeded with a layer of endothelial cells and cultured further. In regions where the matrix is resorbed rapidly, the tissue can expand and become permeated with capillaries that grow from the conduits in the center of the shaded area. Those conduits are 150 to 300 microns in diameter. Each shaded area is 0.5 to 2 mm in diameter. For conduits not embedded in a shaded area, the matrix forming the conduit is relatively slowly-resorbing, ensuring that those blood vessels remain major vessels. While in culture, culture media can also be circulated through the conduits, to help insure that the vessels remain open.

Ideally, devices used for tissue regeneration will have a specific macroscopic shape which can be fashioned to the specific needs of a patient. For example, in mandibular replacement a missing piece of the jaw bone on one side of the patient will be fabricated to exactly match existing bone on the undamaged side by inputting an MRI image of the existing bone into the CAD program which fabricates the device. Further, the devices will ideally have a specific tailored microstructure of interconnected pores and channels for tissue ingrowth where the pores and channels are of precisely defined size, shape, surface chemistry and position within three dimensions. For example, in the case of bone ingrowth, there may be large longitudinal channels for ingrowth of bone and blood vessels from the adjoining bone and smaller transverse channels for ingrowth of blood vessels from the periosteal tissue.

For microstructures tailored to soft tissues it is undesirable to have an inorganic powder as a component of the final device. However, printing a solution of a polymer such as PLA in chloroform or methylene chloride onto an inorganic powder bed or onto a bed of mixed polymer/inorganic is a technique for creating increased porosity in the final device if a water-soluble inorganic powder such as sodium chloride is used. The organic solvents can be removed by vacuum treatment, as is routinely done with manufacture of commercial drug-delivery devices. Supercritical carbon dioxide can also be used as a safe solvent to remove traces of chlorinated solvents. Solvent removal can be facilitated by allowing each layer to dry during the printing process, thereby reducing the length of time required under vacuum for subsequent solvent removal from the device.

After a first layer of powder is spread or placed in the bed of the SFF device, a binder is printed at those locations where it is desired to have walls. The places where no binder is printed become channels or voids when the powder is removed at the end of the process. For long-bone fracture repair devices, a preferred design is to have straight channels of approximately 60 to 300 microns in diameter with approximately 60 to 150 micron walls running the length of the device end-to-end to allow the neighboring bone to grow into the device, and transverse channels of approximately 60 to 100 microns in diameter which will allow ingrowth of blood vessels from the periosteal region, or as described elsewhere herein. Although the transverse channels need not be as numerous as the longitudinal channels from the perspective of the need for blood vessels to grow in, the overall void fraction of the device should remain at greater than 80%. It may be desirable to have transverse walls as thin as 100 microns. The outermost layer may also be designed to prevent excessive tissue ingrowth from the periosteal region, by limiting the number of internal channels which are accessible.

Formation of Blood Vessels

Blood vessels are designed to imitate the parameters of the naturally occurring vascular structure. The diameter of the lumens is increased to compensate for the thickness of the subsequently seeded endothelial cells proliferate to cover the lumen walls. In the preferred embodiment using biodegradable polymer to form the matrix, the matrix eventually degrades to leave only the seeded cells forming blood vessels that are virtually indistinguishable from natural blood vessels. Standard methodology is unable to accomplish the necessary level of detail required to form blood vessel equivalents; this is not a problem with the solid free form techniques since the level of resolution is so small. The blood vessel lumens are interconnected throughout the matrix so that one or more inlets can be anastomized to one or more arteries at the time of implantation, and one or more outlets anastomized to one or more veins. It is preferred to have multiple internal connections and few ports requiring surgical connections at the time of implantation, although such surgery is completely routine for transplantation surgeons who implant transplanted tissues such as livers, lungs, hearts, and other tissues. The connections are made in the same manner as more conventional prosthetic pieces are inserted into blood vessels, esophagus or other tubular structures.

As used herein, "arteries" and "veins" refers to all sizes of blood vessels which branch that could lead into or out of a capillary network.

The present invention is further illustrated by the following non-limiting example of a process for construction of a tissue regeneration matrix using 3DP.

EXAMPLE 1

Production of A Tissue Regeneration Matrix

A tissue regeneration device was printed using 3 DP of a PLLA powder sieved to the 45 to 75 micron range.

The build strategy, shown schematically in FIGS. 3a and 3b, was as follows:

First to Sixth layers: Print a 1×3 cm sheet

Figure 3A:
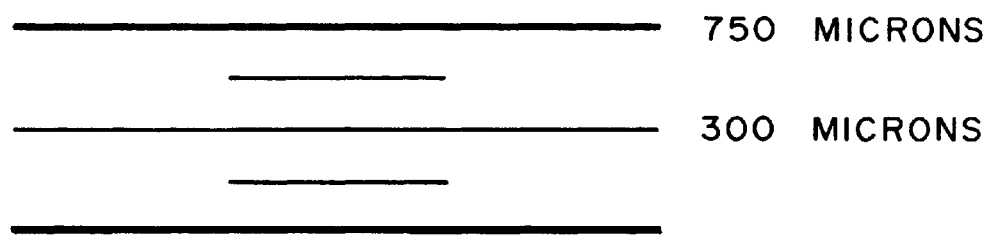
FIGS. 3a and 3b are schematics of the build plan of a polymeric device for generation of tissue having vascular structures contained therein.

Seventh to Seventeenth layers: print as shown in FIG. 3a, with a 750 micron line along the length of both outer edges to form the outer wall, a 300 micron line down the entire center and 300 micron line running down the middle between the center 300 micron line and outer 750 micron line.

Figure 3B:
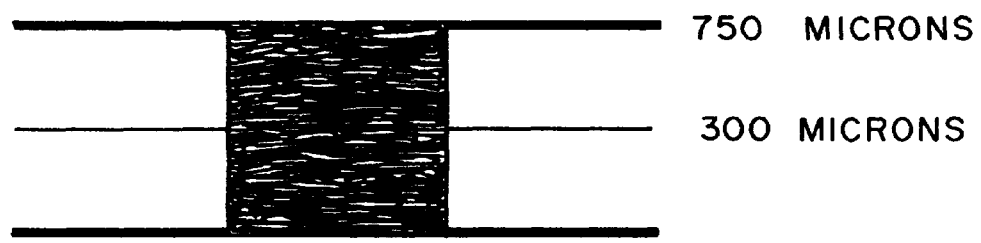

Eighteenth to Nineteenth layers: print as shown in FIG. 3b, with a 300 micron line down the center and a central 1 cm×1 cm sheet.

Twenty to Thirty-first layers: repeat layer 7.

Thirty-second to Thirty-third layers: repeat layer 1.

Thirty-fourth to Forty-fifth layers: repeat layers 18 and 19.

Forty-eighth to Fifty-ninth layers: repeat layer 7.

Sixtieth to Sixty-seventh layers: repeat layer 1.

The resulting device is characterized by walls having a diameter of 300 microns and 500 micron diameter channels.

EXAMPLE 2

Co-Culture of Endothelial Cells and Hepatocytes on a Three-Dimensional Polymer Scaffold Bovine endothelial cells were co-cultured with rat hepatocytes on a device made as described in Example 1.

Methods and Materials

Bovine aortic endothelial cells were harvested from bovine aorta using standard explained techniques and expanded in culture in DMEM (Dulbeccos Modified Eagles Medium), 10% fetal bovine serum, and 1% antibiotic solution. The cells were then trypsinized and counted. Matrices soaked in media were seeded with cells, the cells allowed to attach for one hour, then placed in media. The media was changed after 2 days and then every 1 to 2 days thereafter. Hepatocytes were isolated from rat livers by standard perfusion techniques. The cells were counted and their viability was checked. Two sterile polymer constructs made as described in Example 1 were seeded with $1\times10^6$ hepatocytes and endothelial cells and two polymer constructs were seeded with $1\times10^7$ hepatocytes and endothelial cells were seeded onto 2 polymer constructs. The cells were allowed to attach to the polymer for one hour and then media was added and changed daily thereafter for the first two weeks and then every one or two days thereafter.

Acetylated Low Density Lipoprotein was used to label the endothelial cells two weeks-after the co-cultures were seeded. The constructs were assessed using histological sections and electron microscopy.

Results

Figure 4A:
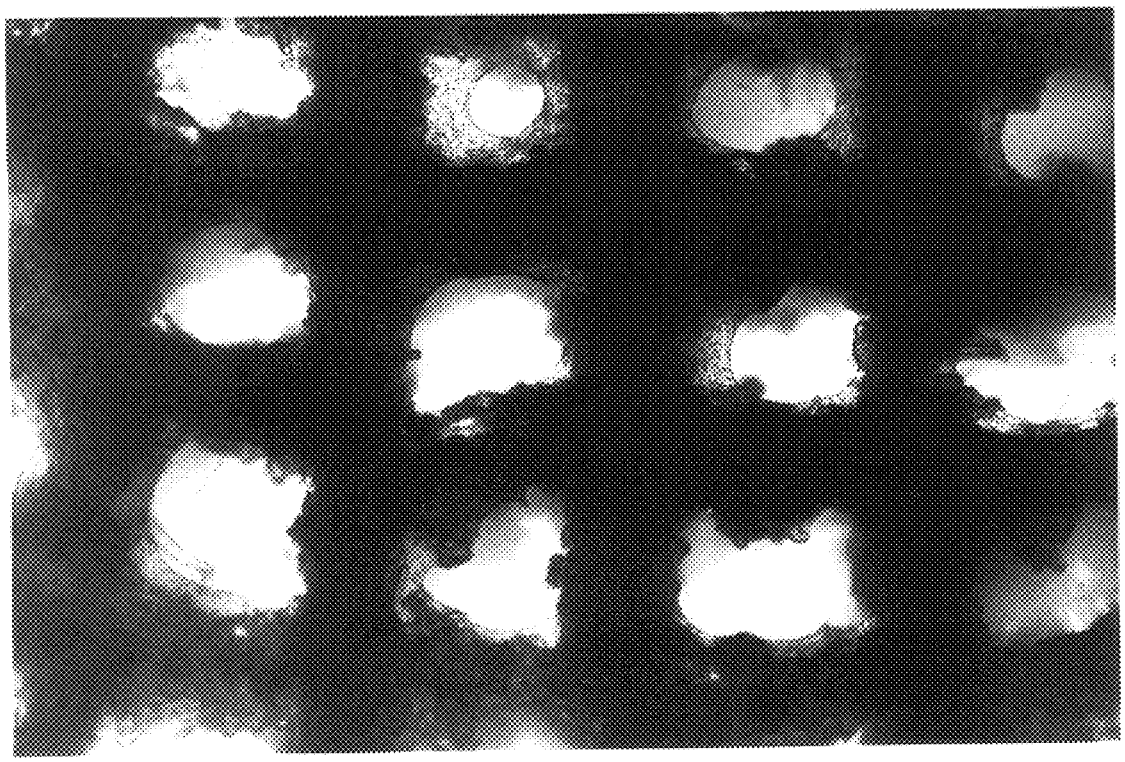
FIGS. 4a, 4b, 4c and 4d are photomicrographs of polymer matrix seeded with rat hepatocytes and bovine endothelial cells.
Figure 4B:
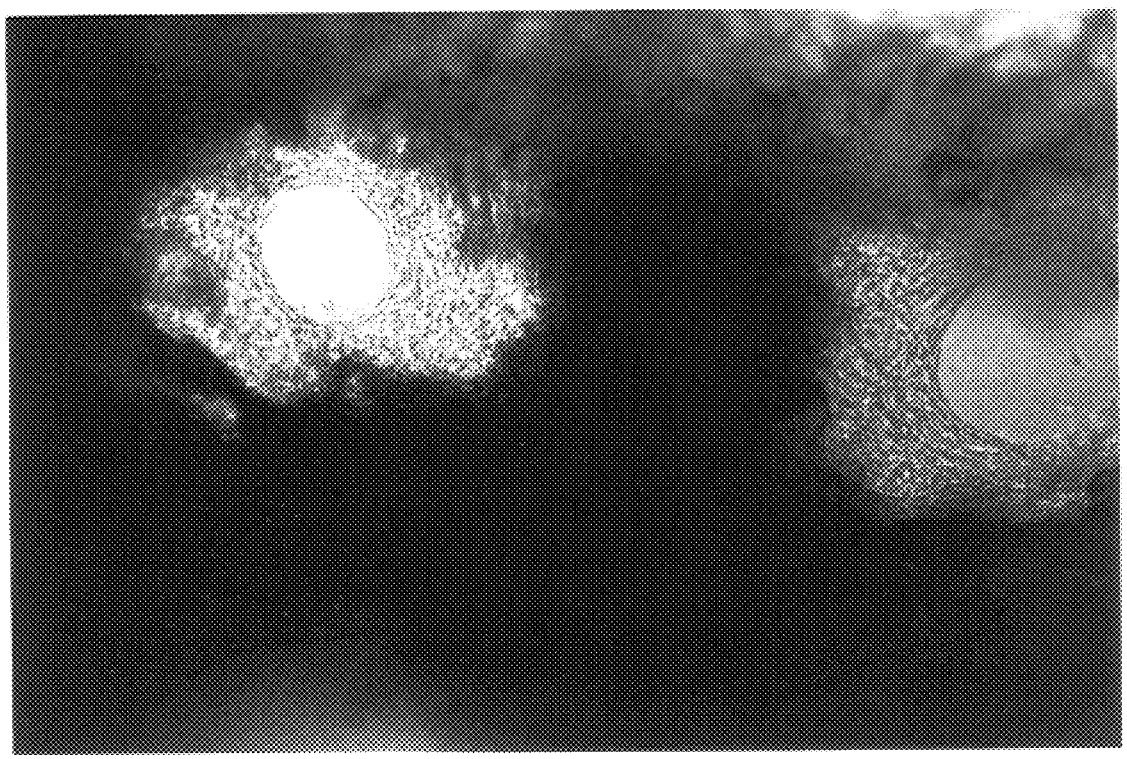
Figure 4C:
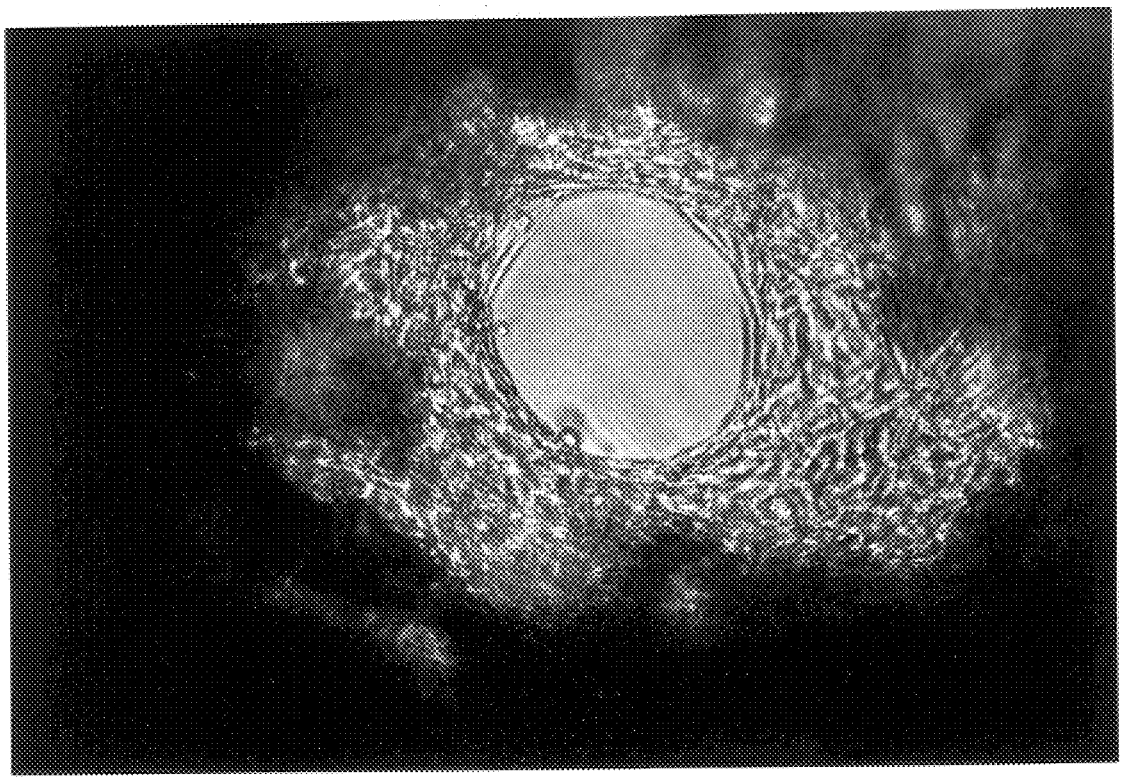
Figure 4D:
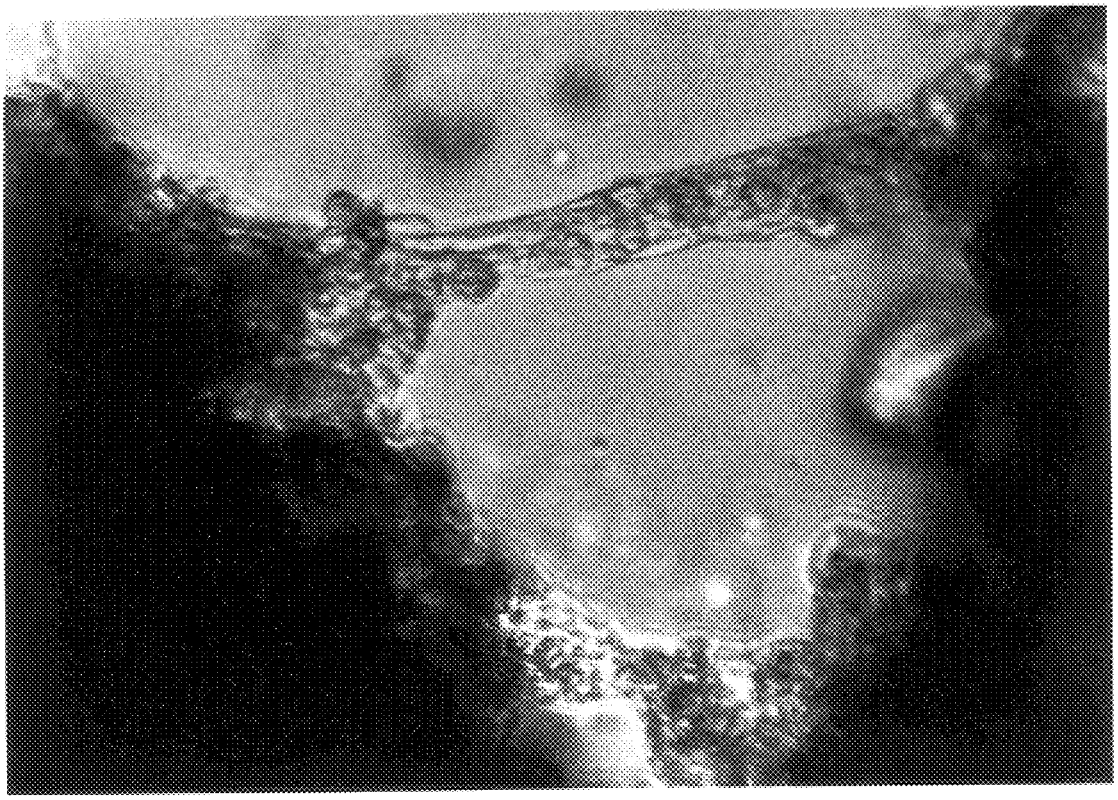

The bovine aortic endothelial cells were attached along the channels of the polymer scaffold soon after seeding. FIG. 4a is photomicrograph of the polymeric matrix seeded with the bovine endothelial cells after two weeks in culture. After two weeks in culture, the endothelial cells began to line the channels gradually smoothing out the rough surface and round out the square channels of the three-dimensional polymer. This is shown in higher magnification in FIGS. 4b and 4c. As most clearly shown in FIG. 4c, after two weeks in vitro, the endothelial cells appear to be laying down a matrix with the second cell type, hepatocytes, adherent to the matrix. When viewed with fluorescent microscopy the LDL labeled endothelial cells appeared to be covering the entire surface of the polymer and lining the channels of the polymer. As shown in FIG. 4d, after a month in culture, the LDL labeled endothelial cells appear to be forming bridges across the matrix channels, with the second rounded cell-type (hepatocytes) adherent to the matrix and adjacent the bridges, histologically similar to that which is found in normal rat livers.

Modifications and variations of the method and compositions described herein will be obvious to those skilled in the art from the foregoing detailed description. Such modifications and variations are intended to come within the scope of the appended claims.

We claim:

1. A method for making devices for tissue regeneration comprising using a solid free-form fabrication method to sequentially form layers of a biocompatible material into a matrix having
    (a) interconnected pores extending throughout the matrix wherein the interconnected pores are for seeding with cells, and
    (b) interconnected lumens within the matrix having openings for connection to ducts within tissue in a patient.

2. The method of claim 1 comprising forming interconnected lumens within the matrix which can be connected to blood vessels.

3. The method of claim 1 comprising forming interconnected lumens within the matrix which can be connected to ducts selected from the group consisting of lymph ducts, exocrine function ducts, excretory ducts, and ducts for neural ingrowth.

4. The method of claim 1 wherein the solid free-form fabrication method is three dimensional printing, comprising
    a) spreading a first dispersion of a biocompatible polymer or composite powder onto a bed,
    b) printing a layer comprising a second dispersion of biocompatible polymer or composite powder in a solvent which binds the first biocompatible polymer or composite powder to the second biocompatible polymer or composite powder at locations where it is desired to have walls, and
    c) repeating step b until the desired matrix is made.

5. The method of claim 1 wherein the solid free-form fabrication method is ballistic particle manufacturing or fusion deposition modeling and polymeric material is applied to a platform in layers to form a polymeric device.

6. The method of claim 1 wherein the solid free-form fabrication method is selective laser sintering comprising applying polymeric particles to a platform and fusing selected area of the polymeric particles with a laser.

7. The method of claim 1 wherein the solid free-form fabrication method is stereo-lithography comprising photopolymerizing selected areas of a bath of photopolymerizable prepolymer or monomers.

8. The method of claim 1 wherein the matrix is formed of biodegradable polymer.

9. The method of claim 8 wherein structural elements having a longer rate of degradation than the matrix-forming material or which are not biodegradable are incorporated into the matrix.

10. The method of claim 1 wherein the texture is altered or surface active agents are applied to the device walls to control cell adhesion to and within the device.

11. The method of claim 10 wherein the matrix is made by three dimensional printing of a binder onto a powder bed where a solution containing surface-active agents is printed into the regions or lines of the powder bed in between where the binder is printed.

12. The method of claim 10 wherein the outer surface of the matrix is modified with a surface active agent which prevents adhesion of cells.

13. The method of claim 1 further comprising seeding the device with dissociated cells.

14. The method of claim 2 further comprising seeding the lumens with dissociated endothelial cells and culturing the device until the cells form a confluent layer on the walls of the lumens.

15. The method of claim 14 further comprising seeding other regions of the matrix with cells forming tissue.

16. A medical device for tissue regeneration formed using a solid free-form fabrication method comprising a matrix of successive layers of a biocompatible material, wherein the layers create
    (a) interconnected pores or lumens extending throughout the matrix wherein the interconnected pores or lumens are for seeding with cells, and
    (b) interconnected lumens within the matrix having openings for connection to ducts within tissue in a patient.

17. The device of claim 16 comprising interconnected lumens within the matrix which can be connected to blood vessels.

18. The device of claim 16 comprising interconnected lumens within the matrix which can be connected to ducts selected from the group consisting of lymph ducts, exocrine function ducts, excretory ducts, and ducts for neural ingrowth.

19. The device of claim 16 wherein the solid free-form fabrication method is three dimensional printing, comprising
    a) spreading a first dispersion of a biocompatible polymer or composite powder onto a bed,
    b) printing a layer comprising a second dispersion of biocompatible polymer or composite powder in a solvent which binds the first biocompatible polymer or composite powder to the second biocompatible polymer or composite powder at locations where it is desired to have walls, and
    c) repeating step b until the desired matrix is made.

20. The device of claim 16 wherein the solid free-form fabrication method is ballistic particle manufacturing or fusion deposition modeling and polymeric material is applied to a platform in layers to form a polymeric device.

21. The device of claim 16 wherein the solid free-form fabrication method is selective laser sintering comprising applying polymeric particles to a platform and fusing selected area of the polymeric particles with a laser.

22. The device of claim 16 wherein the solid free-form fabrication method is stereo-lithography comprising photopolymerizing selected areas of a bath of photopolymerizable prepolymer or monomers.

23. The device of claim 16 wherein the matrix is formed of biodegradable polymer.

24. The device of claim 16 wherein structural elements having a longer rate of degradation than the matrix-forming material or which are not biodegradable are incorporated.

25. The device of claim 16 wherein the texture is altered or surface active agents are applied to the device walls to control cell adhesion to and within the device.

26. The device of claim 25 wherein the matrix is made by three dimensional printing of a binder onto a powder bed where a solution containing surface-active agents is printed into the regions or lines of the powder bed in between where the binder is printed.

27. The device of claim 25 wherein the outer surface of the matrix is modified with a surface active agent which prevents adhesion of cells.

28. The device of claim 16 further comprising bioactive agent.

29. The device of claim 16 wherein the device is formed by a method that builds a complex three dimensional device as a series of two dimensional layers.

30. The device of claim 29 wherein the layers are between 2 microns and 1 mm in thickness.

31. The device of claim 16 wherein the pores or lumens have a diameter of between 150 and 300 microns.

32. The device of claim 16 further comprising seeding the device with dissociated cells.

33. The device of claim 17 further comprising dissociated endothelial cells seeded onto the walls of the pores or lumens.

34. The device of claim 33 further comprising cells forming tissue seeded onto other regions of the matrix.

35. The device of claim 18 further comprising cells forming tissues seeded therein.

36. The device of claim 16 wherein the polymeric material includes a bioactive agent.

* * * * *